Figure 1:
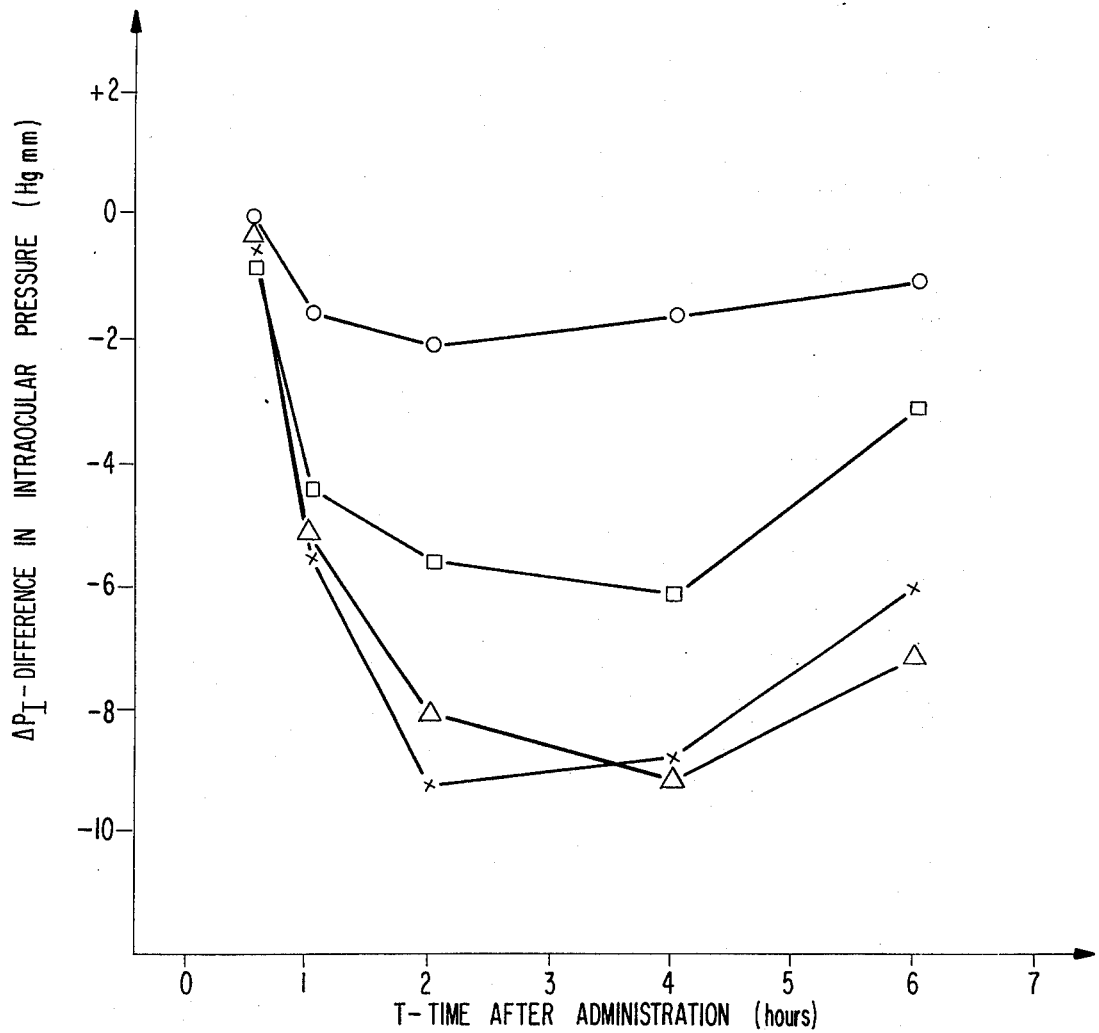

United States Patent [19]

Windheuser

[11] 3,959,485
[45] May 25, 1976

[54] METHOD OF REDUCING INTRAOCULAR PRESSURE IN WARM-BLOODED ANIMALS

[75] Inventor: John J. Windheuser, Lawrence, Kans.

[73] Assignee: Interx Research Corporation, Lawrence, Kans.

[22] Filed: Apr. 10, 1975

[21] Appl. No.: 566,744

[52] U.S. Cl. .............................................. 424/311
[51] Int. Cl.² ........................................ A61K 31/22
[58] Field of Search ................................... 424/311

[56] References Cited
UNITED STATES PATENTS
3,868,461   2/1975   Hussain et al. .................... 424/311

*Primary Examiner*—Norman A. Drezin
*Attorney, Agent, or Firm*—Charles N. Blitzer

[57] ABSTRACT

The intraocular pressure of a warm-blooded animal is substantially reduced by administering topically to the eye thereof, a therapeutically effective amount of a compound of the formula:

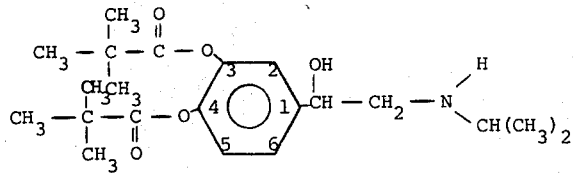

or a pharmaceutically acceptable acid addition salt thereof.

7 Claims, 1 Drawing Figure

- ○ — d-ISOPROTERENOL HYDROCHLORIDE 0.5%
- △ — 3,4-DIPIVALOXY-d,l-α-ISOPROTERENOL HYDROCHLORIDE 0.5%
- □ — 3,4-DIPIVALOXY-d,l-α-ISOPROTERENOL HYDROCHLORIDE 0.25%
- × — d-ISOPROTERENOL HYDROCHLORIDE 3.5%

METHOD OF REDUCING INTRAOCULAR PRESSURE IN WARM-BLOODED ANIMALS

BACKGROUND OF THE INVENTION

1. FIELD OF THE INVENTION

The present invention relates to 3,4-dipivaloxy-α-[(isopropylamino)methyl]benzyl alcohol and its use in the treatment of glaucoma in warm-blooded animals, e.g., humans. More specifically, the present invention relates to the use of the above-mentioned compound in lowering intraocular pressure without initiating attendant cardiac excitatory activity.

2. DESCRIPTION OF THE PRIOR ART

Recently, the use of 3,4-dihydroxy-α-[(isopropylamino)methyl]benzyl alcohol (commonly known as "isoproterenol") in the treatment of glaucoma has been disclosed. See, Netherlands Patent 7,308,193.

Isoproterenol is a well-known sympathomimetic amine which acts almost exclusively on the β-receptors of the postganglionic adrenergic nerves in the sympathetic nervous system and, therefore, the administration of isoproterenol generally produces, among other things, a cardiac excitatory action manifested by tachycardia, palpitation and an increase in the force of contraction of the heart muscle, dilation of vascular beds supplying skeletal muscle, and relaxation of bronchial muscle. As a consequence of the foregoing, while isoproterenol may adequately reduce intraocular pressure in a patient suffering from glaucoma, the inherent cardiac disadvantages associated with this compound as described earlier has substantially precluded its widespread acceptance as an antiglaucoma agent.

As one can appreciate, glaucoma is generally an illness of the elderly. Consequently, the fact that isoproterenol will accentuate cardiac action to such an extent that resultant tachycardia and palpitation become undesirable side effects precludes its use as an effective anti-glaucoma agent in a vast majority of patients.

Moreover, because isoproterenol is relatively lipophobic, it does not readily pass through the ophthalmic membrane (eye). As such, more of the compound is required to achieve a therapeutic effect but at the expense of great ophthalmic pain to the patient.

Finally, isoproterenol causes mydriasis (pupil enlargement) concurrently and/or subsequent to lowering intraocular pressure, which results in temporary vision impairment.

It is, therefore, obviously apparent that a need exists for a useful derivative of isoproterenol which possesses anti-glaucoma activity, while remaining essentially free from the unwanted cardiovascular disadvantages described above.

SUMMARY OF THE INVENTION

Accordingly, it is the primary object of the present invention to provide a means to reduce the intraocular pressure of a warm-blooded animal (e.g., a human) in the treatment of glaucoma.

It is another object of the present invention to provide a means to reduce the intraocular pressure of a warm-blooded animal in the treatment of glaucoma without inducing any accentuated cardiac action such as tachycardia and/or palpitation.

It is still another object of the present invention to produce a substantially lipophilic form of isoproterenol which will readily penetrate the eye such that patient ophthalmic pain, mydriasis and therapeutic dose can be diminished.

All of the foregoing objects are readily attained with a compound of the formula:

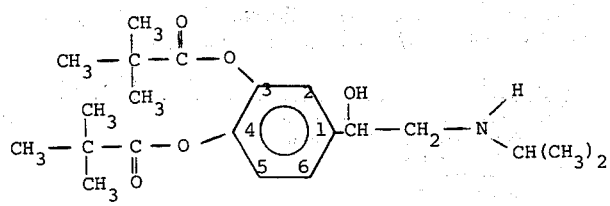

or a pharmaceutically acceptable acid addition salt thereof.

The compound identified above, 3,4-dipivaloxy-α-[(isopropylamino)methyl]benzyl alcohol (3,4-dipivaloxy-α-isoproterenol) is the subject matter of United States Patent application, Ser. No. 308,771, filed Nov. 22, 1972 and now U.S. Pat. No. 3,868,461. As such, the subject matter of this patent, in its entirety, is incorporated herein by reference.

The phrase "pharmaceutically acceptable acid addition salt" as used herein generally includes the non-toxic acid addition salts of the compound referred to above, formed with non-toxic inorganic or organic acids. For example and without limitation, the salts include those derived from inorganic acids such as hydrochloric acid, hydrobromic acid, sulfuric acid, sulfamic acid, phosphoric acid, nitric acid, and the like; and the salts prepared from organic acid such as acetic acid, propionic acid, succinic acid, glycollic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicyclic acid, sulfanilic acid, fumaric acid, toluene-sulfonic acid, etc.

The compound described above encompasses (1) 3,4-dipivaloxy-d-α-[(isopropylamino)methyl]benzyl alcohol, (2) 3,4-dipivaloxy-1-α-[(isopropylamino)methyl]benzyl alcohol, and (3) 3,4-dipivaloxy-d,1-α-[(isopropylamino)methyl]benzyl alcohol. That is, either one of the optical rotary forms of this compound can be employed or racemic mixture containing both.

The compound of the instant invention and its pharmaceutically acceptable acid addition salts can be used by the pharmaceutical and/or veterinary arts for reducing the intraocular pressure in warm-blooded animals in a variety of topical ophthalmic pharmaceutical preparations. In these preparations, the compound and its pharmaceutically acceptable acid addition salts are administrable in combination with any standard acceptable ophthalmic vehicle including conventional phosphate buffer vehicle systems, isotonic boric acid vehicles, isotonic sodium chloride vehicles, isotonic sodium borate vehicles, and the like. Such can be ascertained by simply referring to the text entitled "REMINGTON'S PHARMACEUTICAL SCIENCES," Fourteenth Edition (1970).

Exemplary of a typical method for preparing an ophthalmic composition containing 3,4-dipivaloxy-1-α-[(isopropylamino)methyl]benzyl alcohol, salt, sodium cloride, chlorobutanol, oxime sulfate and distilled water is as follows: First, a measured quantity of chlorobutanol is dissolved in 500 ml of distilled water with stirring and optionally using gentle heat to form a solution. Then, sodium chloride, oxime sulfate and 3,4-dipivaloxy-1-α-[(isopropylamino)methyl]benzyl alcohol bitartrate is added and the solution stirred until clear. Next, distilled water is added to the liter mark and the ophthalmic solution is filtered through a conventional filter having a 0.2 to 0.4 micron pore size. The solution will have a shelf-life stability of three years at 4°C and its compositional form is as follows:

| Ingredients: | Per liter, gm. |
|---|---|
| 3,4-dipivaloxy-1-α-[(isopropylamino)methyl]benzyl alcohol bitartrate | 2.0 |
| Sodium chloride | 8.0 |
| Chlorobutanol | 5.0 |
| Oxime sulfate | 0.1 |
| Distilled water, q.s. 1 liter. | |

A second pharmaceutical formulation similar to the formulation prepared immediately above is made by following that procedure except that the amount of 3,4-dipivaloxy-1-α-[(isopropylamino)methyl]benzyl alcohol bitartrate is increased to 10 grams and 2% phenylethyl alcohol is used as the preservative.

Normally, the amount of active compound per ophthalmic vehicle will range anywhere from 0.1 microgram to 10.0 grams, and the like. Naturally, it is obvious that amounts will vary with the volume of ophthalmic vehicle employed.

The dose administered, whether a single dose or a daily dose, will, of course, vary with the needs of the individual. However, the dosage administered is not subject to definite bounds, but it will usually be an effective amount, or the equivalent on a molar basis of the pharmacologically active form produced upon the metabolic release of the active drug to achieve its desired pharmacological and physiological effect. Normally, the medical dose for warm-blooded mammals, including humans and primates will be in the range of about 0.01 to 10.0% and the like, 0.025 to 4.0% being preferred. Administration of an ophthalmic solution containing the active compound to the eye can be made via eyedrop, ophthalmic aerosol, etc.

Without further elaboration, it is believed that one of ordinary skill in the art can, using the preceding description, utilize the present invention to its fullest extent. The following preferred specific embodiments are, therefore, to be construed as very illlustrative, and not limitative of the remainder of the specification and claims in any way whatsoever.

EXAMPLE I — EVALUATION OF CARDIAC EXCITATORY ACTIVITY (Reproduced from United States Patent 3,868,461)

First, adult male rats or guinea pigs are fitted with chronically implanted aortic catheters; Ruben D. Bunag, Journal of Laboratory and Clinical Medicine, 78, 675–682 (October, 1971), St. Louis, Missouri. The indwelling catheter is then attached to a device for recording pressure changes. (A Statham P23Gb strain gage, for example.)

The test compound is administered as an intravenous solution or by means of a nebulized mist. The observed heart rate and blood pressures are set forth in Table I below:

TABLE I

| Compound | Dose By Inhalation | Change In Heart Rate | Change In Blood Pressure |
|---|---|---|---|
| 3,4-dihydroxy-α-[(isopropylamino)methyl]benzyl alcohol hydrochloride | 0.4% | 100 Beats/min | 30 mm Hg |
| 3,4-dipivaloxy-α-[(isopropylamino)methyl]benzyl alcohol hydrochloride | 0.4% | 2 Beats/min | 0–5 mm Hg |
| 3,4-dihydroxy-α-[(isopropylamino)methyl]benzyl alcohol hydrochloride | 1.25 μg/ml I.V. | 50 Beats/min | |
| 3,4-dipivaloxy-α-[(isopropylamino)methyl]benzyl alcohol hydrochloride | 10 μg/ml I.V. | 0 Beats/min | |

EXAMPLE II — BIOLOGICAL PROFILE

In FIG. 1 accompanying the instant application, there is a biological profile of the effect of (1) a 0.5% solution of d-isoproterenol hydrochloride, (2) a 0.5% solution of 3,4-dipivaloxy-d,l-α-isoproterenol hydrochloride, (3) a 0.25% solution of 3,4-dipivaloxy-d,l-α-isoproterenol hydrochloride, and (4) a 3.5% solution of d-isoproterenol hydrochloride on intraocular pressure. As can be readily observed, on a one to one comparison, 3,4-dipivaloxy-d,l-α-isoproterenol hydrochloride is far superior to d-isoproterenol hydrochloride in reducing intraocular pressure.

From the foregoing description, one of ordinary skill in the art can easily ascertain the essential characteristics of the instant invention, and without departing from the spirit and scope thereof, can make various changes and modifications of the invention to adapt it to various usages and conditions. As such, these changes and modifications are properly, equitably, and intended to be, within the full range of equivalence of the following claims.

What I claim is:

1. A method for lowering elevated intraocular pressure in a warm-blooded animal suffering from glaucoma which comprises topically administering to the eye thereof, a therapeutically effective amount of a compound selected from the group consisting of 3,4-dipivaloxy-α-[(isopropylamino)methyl]benzyl alchohol or a nontoxic pharmaceutically acceptable acid addition salt thereof.

2. The method of claim 1, wherein said compound is in racemic form.

3. The method of claim 1, wherein said compound is in the d form.

4. The method of claim 1, wherein said compound is in the l form.

5. The method of claim 1, wherein said compound is administered in combination with a pharmaceutically acceptable ophthalmic carrier.

6. The method of claim 5, wherein said compound is present in a therapeutically effective amount ranging from 0.01 to 10.0%.

7. The method of claim 6, wherein said therapeutically effective amount is within the range of from 0.025 to 4.0%.

* * * * *